United States Patent [19]

Takahashi et al.

[11] Patent Number: 5,399,711
[45] Date of Patent: Mar. 21, 1995

[54] THIOMARINOL COMPOUNDS

[75] Inventors: Shuji Takahashi; Hideyuki Shiozawa; Katsumi Fujimoto; Yuji Iwano; Koichi Hirai; Akio Torikata, all of Tokyo; Takeshi Kagasaki, Iwaki; Kaneo Ogawa, Iwaki; Yoshiharu Sakaida, Iwaki; Kentaro Kodama; Akira Ishii, both of Tsukuba, all of Japan

[73] Assignee: Sankyo Company, Limited, Tokyo, Japan

[21] Appl. No.: 124,396

[22] Filed: Sep. 20, 1993

[30] Foreign Application Priority Data

Sep. 18, 1992 [JP] Japan ................ 4-248970
Nov. 2, 1992 [JP] Japan ................ 4-294170
Nov. 5, 1992 [JP] Japan ................ 4-295695

[51] Int. Cl.$^6$ ............................ C07D 495/04
[52] U.S. Cl. ....................... 548/453; 435/119
[58] Field of Search ............................ 548/453

[56] References Cited

FOREIGN PATENT DOCUMENTS

| | | |
|---|---|---|
| 0254223 | 1/1988 | European Pat. Off. . |
| 0512824A1 | 11/1992 | European Pat. Off. . |
| 52-102279 | 8/1977 | Japan . |
| 54-12375 | 1/1979 | Japan . |
| 54-90179 | 7/1979 | Japan . |
| 54-103871 | 8/1979 | Japan . |
| 54-125672 | 9/1979 | Japan . |
| 59-501950 | 11/1984 | Japan . |
| 63-27484 | 2/1988 | Japan . |
| 1565083 | 4/1980 | United Kingdom . |
| 84/01775 | 5/1984 | WIPO . |

OTHER PUBLICATIONS

Patent Abstracts of Japan of JP 54 125 672, vol. 3, No. 147 (1979).
Patent Abstracts of Japan of JP 54 103 871, vol. 3, No. 123 (1979).
Chain et al, "Pseudomonic Acid. Part 1. The Structure of Pseudomonic Acid A, a Novel Antibiotic produced by *Pseudomonas Fluorescens*", 1977, pp. 294–309, *J. Chem. Soc. Perkin Trans, I.*

*Primary Examiner*—David B. Springer
*Attorney, Agent, or Firm*—Frishauf, Holtz, Goodman & Woodward

[57] ABSTRACT

Two thiomarinol derivatives, which have antibacterial and anti-mycoplasmal properties, are obtainable from microorganisms of the genus Alteromonas and are named "thiomarinol B" and "thiomarinol C". Thiomarinol B can also be prepared by the oxidation of thiomarinol.

8 Claims, No Drawings

THIOMARINOL COMPOUNDS

BACKGROUND TO THE INVENTION

The present invention relates to certain new derivatives of thiomarinol and provides processes for their preparation and methods and compositions using them as antibacterial agents.

Thiomarinol is described, for example, in European Patent Publication No. 512 824, published before the application date hereof but after the priority dates. It may be represented by the formula (A):

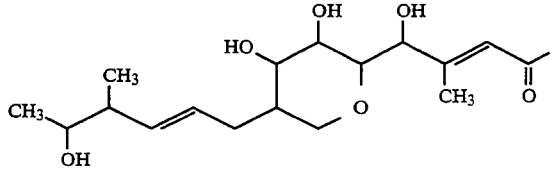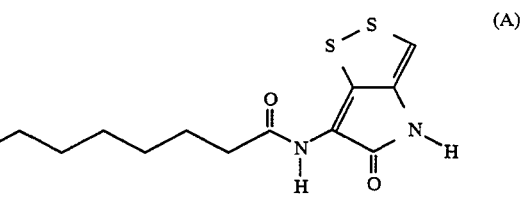

(A)

It is produced by fermentation by microorganisms of the genus Alteromonas, especially *Alteromonas rava* strain SANK 73390. We have now discovered two derivatives of thiomarinol, which have similar types of antibiotic activity to the original thiomarinol.

Organisms of the genus Alteromonas can be isolated from sea water, and some have been shown to produce compounds of potential therapeutic use. For example, a compound known as bisucaberin has been obtained from one species of Alteromonas, and has been shown to exhibit antitumor activity (Japanese Patent Kokai Application Number Sho 63-27484).

With respect to the structure of thiomarinol, several antibiotic substances having similar structures are known, and these may be divided into four groups.

The first group comprises the pseudomonic acids, first isolated from Pseudomonas spp. These include pseudomonic acid A [produced by *Pseudomonas fluorescens*, disclosed in J. Chem. Soc. Perkin Trans. I, 294 (1977)], pseudomonic acid B [ibid, 318 (1977)], pseudomonic acid C [ibid, 2827 (1982)] and pseudomonic acid D [ibid, 2655 (1983)]. Pseudomonic acid A is marketed under the name "Bactroban" (Beecham, registered trade mark) in the form of a 2% dermatological ointment for antibacterial use. However, all of these prior art compounds have weaker antibacterial activities than do the thiomarinol derivatives of the present invention.

The second group of substances sharing a similarity of structure with the compounds of the invention comprises that group which includes the antibiotics holomycin [Helv. Chim. Acta, 42, 563 (1959)], pyrrothine [J. Am. Chem. Soc., 77, 2861 (1955)], thiolutin [Angew. Chem., 66, 745 (1954)], aureothricin [J. Am. Chem. Soc., 74, 6304 (1952)], and others. These antibiotics are typically produced by actinomycetes, and are characterized by a sulfur-containing chromophore. Xenorhabdins I–V are substances related to holomycin, and have also been isolated from bacteria (disclosed in WO 84/01775).

Various studies on derivatives of these two groups have been performed, but we are not aware of any disclosure of a substance having a molecular structure similar to that of the thiomarinols, or which is characterized by similar properties.

The third group of compounds is disclosed in publications such as Japanese Application Kokai Numbers 52-102279, 54-12375, 54-90179, 54-103871 and 54-125672, which disclose pseudomonic acid derivatives wherein the terminal carboxylic acid is replaced by an amide group. These compounds do not exert comparable antibacterial activity and do not exhibit a broad spectrum of antibacterial activity. In fact, these compounds demonstrate a tendency to possess weaker antibiotic activity than that of the original pseudomonic acid.

The fourth group comprises a compound similar to thiomarinol in that it is a physiological substance of marine bacterial origin [Abstracts of Papers from the 200 Year Conference of the Am. Chem. Soc. (August 26–31, 1990), Part 2, ORGN. No. 139]. However, the heterocyclic group bonded to the terminal carbonyl group of this compound is a 2-oxo-3-piperidyl group. It has recently been shown to have antimicrobial activity [Experimentia, Vol. 48, pages 1165–1169 (1992)].

However, the most relevant prior art is thought to be pseudomonic acid A, and all of the thiomarinols, that is the original thiomarinol, thiomarinol B and thiomarinol C, have significantly more potent antibacterial activity than does pseudomonic acid A.

BRIEF SUMMARY OF INVENTION

It is an object of the present invention to provide certain novel derivatives of thiomarinol.

It is a further, and more specific, object to provide such compounds which have excellent antibacterial and anti-mycoplasmal activity.

Other objects and advantages will become apparent as the description proceeds.

In general terms, the present invention provides two new derivatives of thiomarinol, one of which is an S,S-dioxo derivative and is referred to herein as "thiomarinol B", and the other of which is a deoxy derivative and is referred to herein as "thiomarinol C".

The structure of thiomarinol B has not yet been finally determined and it can be seen from the formula of thiomarinol itself [formula (A)] that there are two possible positions for S-oxidation. Thus, thiomarinol B is characterised herein by its physico-chemical properties, as follows:

1) Nature and appearance: Yellow powder.
2) Molecular formula: $C_{30}H_{44}N_2O_{11}S_2$.
3) Molecular weight: 672 (as determined by FAB-MS) "FAB-MS" is Fast Atom Bombardment Mass Spectrometry.
4) High-resolution mass spectrometry: $C_{30}H_{45}N_2O_{11}S_2$ [$(M+H)^+$; as determined by FAB-MS] Found 673.2468 Calculated 673.2465.

5) Elemental analysis: Calculated for $C_{30}H_{44}N_2O_{11}S_2+H_2O$: C, 52.16%; H, 6.71%; N, 4.06%; S, 9.28%. Found: C, 52.34%; H, 6.79%; N, 3.92%; S, 9.02%.

6) Infrared absorption spectrum: $\nu_{max}$ cm$^{-1}$

The infrared absorption spectrum as measured by the potassium bromide (KBr) disc method is as indicated below.

3660, 3503, 3318, 3075, 2966, 2928, 2870, 1704, 1653, 1509, 1467, 1381, 1349, 1299, 1217, 1199, 1152, 1112, 1063, 1047, 1019, 975, 949, 884, 839, 764, 730, 660, 609, 553.

7) Ultraviolet absorption spectrum: $\nu_{max}$ nm ($\epsilon$)

The ultraviolet absorption spectrum as measured in 1-propanol is as indicated below:
377 (2,900), 301 (13,000), 215 (21,000).

The ultraviolet absorption spectrum as measured in 1-propanol+hydrochloric acid is as indicated below:
377 (2,900), 301 (13,000), 223 (17,000).

The ultraviolet absorption spectrum as measured in 1-propanol +sodium hydroxide is as indicated below:
377 (2,900), 301 (13,000), 221 (19,000).

8) Specific rotation: $[\alpha]_D^{25} = +7.7°$ (c=1.0, 1-propanol).

9) High-performance liquid chromatography:
Separation column: Senshu-Pak ODS H-2151 (column diameter 6 mm, length 150 mm, a trade mark for a product of Senshu Scientific Co., Ltd.)
Solvent: 40% v/v aqueous acetonitrile
Flow rate: 1.5 ml/minute
Retention time: 8.4 minutes.

10) $^1$H-Nuclear Magnetic Resonance spectrum: ($\delta$: ppm)

The nuclear magnetic resonance spectrum (360 MHz) as measured in hexadeuterated dimethyl sulfoxide using tetramethylsilane as the internal standard is as indicated below.

11.28 (1H, broad singlet);
10.47 (1H, singlet);
7.23 (1H, singlet);
5.97 (1H, singlet);
5.37 (2H, multiplet);
4.88 (1H, doublet, J=7.5 Hz);
4.61 (1H, broad singlet);
4.43 (1H, doublet, J=7.2 Hz);
4.28 (1H, doublet, J=3.6 Hz);
4.18 (1H, doublet, J=7.2 Hz);
4.02 (2H, triplet, J=6.6 Hz);
3.74 (1H, broad singlet);
3.64 (1H), 3.61 (1H), 3.54 (1H), 3.51 (1H);
3.35 (1H, doublet, J=10.9 Hz);
2.43 (2H, triplet, J=7.3 Hz);
2.12 (1H), 2.09 (1H), 2.03 (1H);
2.02 (3H, singlet);
1.61 (1H), 1.58 (2H), 1.50 (2H), 1.32 (2H), 1.30 (2H), 1.25 (2H);
0.96 (3H, doublet, J=6.3 Hz);
0.92 (3H, doublet, J=6.9 Hz).

11) $^{13}$C-Nuclear Magnetic Resonance spectrum: ($\delta$: ppm)

The nuclear magnetic resonance spectrum (90 MHz) as measured in hexadeuterated dimethyl sulfoxide using tetramethylsilane as the internal standard is as indicated below.

173.5 (singlet), 166.1 (singlet), 165.7 (singlet),
160.8 (singlet), 143.2 (singlet), 134.2 (doublet),
127.8 (doublet), 123.3 (singlet), 115.2 (singlet),
114.4 (doublet), 109.4 (doublet), 76.2 (doublet),
72.4 (doublet), 69.6 (doublet), 69.3 (doublet),
64.3 (triplet), 63.9 (doublet), 63.0 (triplet),
43.2 (doublet), 42.2 (doublet), 34.7 (triplet),
31.9 (triplet), 28.3 (triplet), 28.2 (triplet),
28.1 (triplet), 25.3 (triplet), 24.5 (triplet),
20.0 (quartet), 15.7 (quartet), 15.6 (quartet).

12) Solubility:
Soluble in alcohols, such as methanol, ethanol, propanol and butanol, as well as in dimethyl sulfoxide, dimethylformamide, chloroform, ethyl acetate, acetone and diethyl ether. Insoluble in hexane and water.

13) Thin-layer chromatography:
$R_f$ value: 0.52
Adsorbing agent: Silica gel (Merck & Co., Inc., Art. 5715)
Developing solvent: Methylene chloride:methanol=85:15 by volume.

Another compound of the present invention is thiomarinol C, which can be represented by the following formula (C):

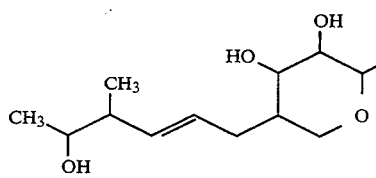 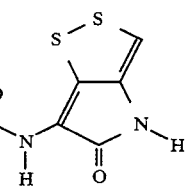

(C)

The invention also provides a process for preparing thiomarinol B or C, which comprises cultivating a thiomarinol-producing microorganism of the genus Alteromonas and isolating thiomarinol B or C from the culture.

The invention also provides a process for the preparation of thiomarinol B by the oxidation of thiomarinol.

The invention also provides a pharmaceutical composition comprising an antibacterial or anti-mycoplasmal agent in admixture with a pharmaceutically acceptable carrier or diluent, wherein the antibacterial or anti-mycoplasmal agent is selected from the group consisting of thiomarinol B and C.

The invention still further provides a method for the treatment or prophylaxis of bacterial or mycoplasmal infections, which method comprises administering an effective amount of an antibacterial or anti-mycoplasmal agent to a mammal, which may be human, suffering from or susceptible to such an infection.

DETAILED DESCRIPTION OF THE INVENTION

Although the structure of thiomarinol B is not certain, it is thought that it is a compound having the formula (B1) or (B2):

The ultraviolet absorption spectrum as measured in methanol or methanol+hydrochloric acid is as indicated below:

388 (9,600), 300 (2,700), 215 (17,000).

The ultraviolet absorption spectrum as measured in methanol +sodium hydroxide is as indicated below:

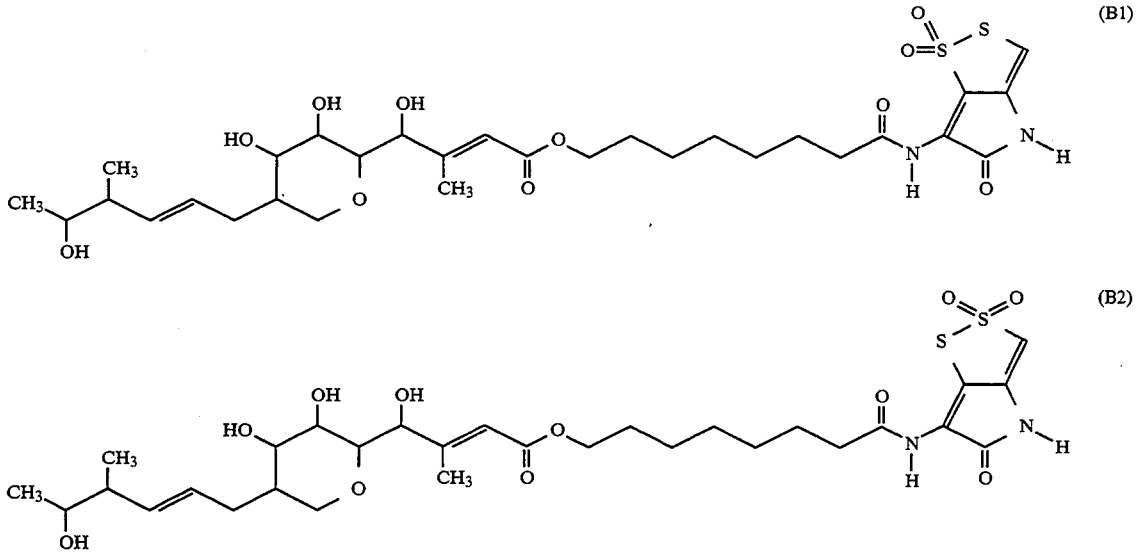

It may be a single one of these compounds or it may be a mixture of the two compounds. In the case of a mixture, the relative proportions may be fixed or they may vary, depending on the method of preparation.

It is clear from the above formula that thiomarinols B and C contain a number of asymmetric carbon atoms and several double bonds. Isomerization is particularly possible at the $\alpha,\beta$-unsaturated carbonyl moiety of the thiomarinols. The thiomarinols can, therefore, form various stereo and geometric isomers. Although these are all represented herein by a single molecular formula, the present invention includes both the individual, isolated isomers and mixtures thereof, including racemates. Where stereospecific synthesis techniques are employed, or optically active compounds are employed as starting materials, individual isomers may be prepared directly; on the other hand, if a mixture of isomers is prepared, the individual isomers may be obtained by conventional resolution techniques.

Since, however, the thiomarinols are normally produced by fermentation or by chemical manipulation of a fermentation product, they will tend to adopt a standard optical configuration. Thus, while other configurations are provided, the natural configuration is preferred.

Thiomarinol C may be characterised by the following physico-chemical properties:
1) Nature and appearance: Yellow powder.
2) Molecular formula: $C_{30}H_{44}N_2O_8S_2$.
3) Molecular weight: 624 (as determined by FAB-MS).
4) Elemental analysis: Calculated for $C_{30}H_{44}N_2O_8S_2+H_2O$: C, 56.05%; H, 7.21%; N, 4.36%; S, 9.97%. Found: C, 56.48%; H, 7.23%; N, 4.30%; S, 9.11%.
5) Infrared absorption spectrum: $\nu_{max}$ cm$^{-1}$ The infrared absorption spectrum as measured by the potassium bromide (KBr) disc method is as indicated below:

3256, 3068, 2928, 2858, 1645, 1596, 1530, 1455, 1384, 1287, 1225, 1151, 1104, 1052, 974, 820, 712.

6) Ultraviolet absorption spectrum: $\nu_{max}$ nm ($\epsilon$)

386 (8,600 ), 205 (49,000 ) .

7) Specific rotation: $[\alpha]_D^{25} = -1.4°$ (c=1.0, methanol).

8) High performance liquid chromatography:

Separating column: Senshu-Pak ODS H-2151 (column size, diameter 6 mm, length 150 mm, Senshu Scientific Co., Ltd.)

Solvent: 40% v/v aqueous acetonitrile
Flow rate: 1.5 ml/minute
Retention time: 11.3 minutes.

9) $^1$H-Nuclear magnetic resonance spectrum: ($\delta$: ppm)

The nuclear magnetic resonance spectrum (360 MHz) as measured in hexadeuterated dimethyl sulfoxide using tetramethylsilane as the internal standard is as indicated below.

10.70 (1H, singlet);
9.81 (1H, singlet);
7.05 (1H, singlet);
5.68 (1H, singlet);
5.37 (1H, multiplet);
5.33 (1H, multiplet);
4.64 (1H, broad singlet);
4.55 (1H, broad multiplet);
4.32 (1H, doublet, J=4.3 Hz);
4.01 (2H, triplet, J=6.6 Hz);
3.67 (1H), 3.62 (1H), 3.58 (1H), 3.49 (1H), 3.35 (1H);
3.18 (1H, broad multiplet);
2.56 (1H, broad doublet, J=14.2 Hz);
2.34 (2H, triplet, J=7.3 Hz);
2.15 (1H);
2.11 (3H, singlet);
2.08 (1H), 2.06 (2H);
1.63 (1H, multiplet);
1.56 (2H, multiplet);
1.51 (2H, multiplet);
1.30 (2H), 1.29 (2H), 1.26 (2H);
0.95 (3H, doublet, J=6.3 Hz);
0.91 (3H, doublet, J=6.9 Hz).

10) $^{13}$C-Nuclear magnetic resonance spectrum: ($\delta$: ppm)

The nuclear magnetic resonance spectrum (90 MHz) as measured in hexadeuterated dimethyl sulfoxide using tetramethylsilane as the internal standard is as indicated below.

171.8 (singlet), 167.9 (singlet), 165.7 (singlet),
157.9 (singlet), 134.2 (doublet), 133.9 (singlet),
133.6 (singlet), 127.6 (doublet), 116.5 (doublet),
115.3 (singlet), 110.4 (doublet), 74.4 (doublet),
69.3 (doublet), 69.2 (doublet), 68.1 (doublet),
64.0 (triplet), 63.0 (triplet), 43.1 (doublet),
42.5 (triplet), 42,0 (doublet), 34.6 (triplet),
32.1 (triplet), 28.4 (triplet), 28.3 (triplet),
28.1 (triplet), 25.2 (triplet), 24.9 (triplet),
20.0 (quartet), 18.6 (quartet), 15.7 (quartet).

11) Solubility:

Soluble in alcohols such as methanol, ethanol, propanol and butanol, as well as in dimethyl sulfoxide, dimethylformamide, chloroform, ethyl acetate, acetone and diethyl ether. Insoluble in hexane and water.

12) Thin layer chromatography:

$R_f$ value: 0.66

Adsorbing agent: Silica gel (Merck & Co., Inc., Art. 5719)

Developing solvent: Methylene chloride:methanol=85:15 by volume.

Thiomarinol B and C may be prepared by culturing a thiomarinol-producing microorganism of the genus Alteromonas, and then collecting the desired thiomarinol B and/or C from the culture medium. Variants of thiomarinol B and/or C possessing the required antibacterial activity may be obtained in a similar manner from other strains or species of Alteromonas which produce the required compound, or they may be obtained by suitable modification of a compound obtained by fermentation as described, or they may be directly chemically synthesised.

In particular, we especially prefer to employ as the microorganism the species *Alteromonas rava* and particularly a recently isolated strain of *Alteromonas rava* to which we have given the strain designation SANK 3390. Strain SANK 73390 is a marine microorganism which was isolated from sea water collected at the seaside of Koina, Minami-Izu Machi, Shizuoka Prefecture, Japan, and this strain has been deposited with the Deposition Institute, Fermentation Research Institute, Agency of Industrial Science & Technology, Ministry of International Trade and Industry, Japan, on Apr. 30, 1991, with the Accession no. FERMBP-3381, under the terms of the Budapest Treaty.

The taxonomical characteristics of *Alteromonas rava* strain SANK 73390 are shown below.

1. Morphological characteristics

*Alteromonas rava* strain SANK 73390 was cultured at 23° C. for 24 hours on Marine Agar (Difco). Subsequent microscopic observation revealed that the cells were rod-like in shape and each was 0.8 to 1.0 μm in diameter and 2.0 to 3.6 μm in length. This strain is gram-negative, and moves by means of a polar monotricous flagellum.

2. Growth on Marine Agar

SANK 73390 was cultured for 24 hours at 23° C. on Marine Agar (Difco). The resulting colonies were observed to be pale grayish yellow in color, opaque, circular, flat and entire. Water-soluble pigment was not formed.

3. Physiological properties (1) Seawater requirement: SANK 73390 requires sea water for growth.

(2) Oxidative-fermentative test (Hugh-Leifson method [J. Bact., 66, 24–26 (1953)], in a medium prepared from artificial sea water): no action on carbohydrate.

(3) Oxidase: +

(4) Catalase: +

(5) Oxygen requirement: aerobic (6) Reduction of nitrate: —

(7) Hydrolysis of starch: +

(8) Decomposition of agar: —

(9) Liquefaction of gelatin: +

(10) DNase production: +

(11) Lipase production: +

(12) Temperature for growth: Poor growth at 4° C., good growth between 17° C. and 26° C., no growth at 35° C.

(13) Growth factor requirement: On the basal medium described in Journal of Bacteriology 107, 268–294 (1971), SANK 73390 requires vitamin-free Casamino Acid.

(14) Assimilation of carbon sources: On the basal medium described in the Journal of Bacteriology 107, 268–294 (1971), additionally comprising 0.1% w/v vitamin-free Casamino Acid, in shaking culture:

TABLE

| | | | |
|---|---|---|---|
| L-Arabinose: | — | D-Ribose: | — |
| D-Xylose: | — | D-Glucose: | + |
| D-Galactose: | — | D-Fructose: | — |
| Maltose: | + | Sucrose: | — |
| Trehalose: | + | Cellobiose: | — |
| Melibiose: | — | Mannitol: | — |
| Sorbitol: | — | Glycerin: | — |
| Sodium acetate: | + | Sodium propionate: | + |

4. Chemotaxonomic character (1) Mol % of guanine and cytosine (G+C content) of DNA: 43.4% (HPLC method)

(2) Quinone system: Ubiquinone Q-8

Taking into account the taxonomical characteristics shown above, *Alteromonas rava* strain SANK 73390 was compared with the strains described in Bergey's Manual of Systematic Bacteriology, Vol. 1 (1984), as well as with those strains described in recent issues of the International Journal of Systematic Bacteriology. We found that *Alteromonas rava* strain SANK 73390 shared certain similarities with *Alteromonas citrea*, another marine microorganism. SANK 73390 and *Alteromonas citrea*, ATCC 29719 (a standard strain), were comparatively cultured, and compared.

Compared to the pale grayish yellow color of SANK 73390, the colonies of ATCC 29719 were greenish yellow in color. SANK 73390 also differed from *Alteromonas citrea* in growth at 4° C., and in the ability to utilize trehalose and sodium propionate as carbon sources. Accordingly, *Alteromonas rava* strain SANK 73390 is a new strain of the new species *Alteromonas rava*, and differs in essential characteristics from the nearest known species deposited with Accession No. ATCC 29719.

The above-described characteristics are typical of SANK 73390. However, it is well known that the characteristics of Alteromonas spp. are changeable, both naturally and artificially. The characteristics defined above define the strain of *Alteromonas rava* as deposited, but are not necessarily typical of other species of Alteromonas, or of strains of *Alteromonas rava*, which are capable of producing thiomarinol or a naturally occurring variant thereof. Such other strains are included within the scope of the invention.

It will be appreciated that SANK 73390, or any other strain capable of producing a thiomarinol or one of its variants, may be sub-cultured or biotechnologically altered or modified to produce an organism with different characteristics. The only requirement is that the resulting organism be capable of producing the required compound.

Such alterations and modifications may take any desired form, or may, for example, be consequent on such considerations as culture conditions. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in Alteromonas spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring Alteromonas plasmid and inserting a desired gene or genes from another source. Natural plasmids may also be modified in any other manner that may be considered desirable.

In order to obtain thiomarinol B and/or C from a culture of a suitable microorganism, the microorganisms should be fermented in a suitable medium. Such media are generally well known in the art, and will frequently be used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include glucose, fructose, maltose, sucrose, mannitol, glycerol, dextrin, oatmeal, rye, corn starch, potato, corn powder, soybean powder, cotton seed oil, syrup, citric acid and tartaric acid, any of which may be employed alone or in combination with one or more others. Typical amounts will be in a range from about 1 to 10% w/v of the amount of medium, although the amount may be varied as desired and in accordance with the desired result.

Suitable nitrogen sources include any substance containing, for example, a protein. Representative examples of nitrogen sources are organic nitrogen sources from animals and plants, and may be extracts from such natural sources as soybean meal, bran, peanut meal, cotton seed meal, casein hydrolysate, fermamine, fish powder, corn steep liquor, peptone, meat extract, yeast, yeast extract, malt extract; and from such inorganic nitrogen sources as sodium nitrate, ammonium nitrate and ammoniumsulfate. As with the carbon source, these may be employed alone or in combination. Suitable amounts are typically within a range from about 0.1 to 6% w/v of the amount of medium.

Suitable nutrient inorganic salts are those which provide trace elements as well as the major constituent of the salt. Preferably, salts should provide such ions as sodium, potassium, ammonium, calcium, magnesium, iron, phosphate, sulfate, chloride and carbonate. Such trace metals as cobalt, manganese and strontium, or salts capable of providing such ions as bromide, fluoride, borate or silicate ions, may also be present.

It will be appreciated that *Alteromonas rava* occurs naturally in sea water, so that, in the absence of indications to the contrary, conditions for its culture will ideally correspond to a marine environment. Thus, trace ions found in the sea are advantageously included in any medium used for the culture of Alteromonas. In particular, it is preferred that the microorganism should be cultured in the presence of sea water, of artificial sea water or of components corresponding to the composition of sea water.

If the microorganism is fermented as a liquid culture, it is preferred that an antifoam agent, such as a silicone oil or vegetable oil, or other suitable surfactant, is employed.

It is preferred that the pH of the culture medium for *Alteromonas rava* strain SANK 73390, when used for the production of thiomarinol B and/or C, is maintained in the region of pH 5.0 to pH 8.0, although the only requirement is that the pH should not prevent growth of the microorganism, or adversely irreversibly affect the quality of the final product. It may be preferred to add an excess of an acid or an alkali to stop fermentation.

*Alteromonas rava* strain SANK 73390, in general, grows at temperatures ranging from 4° C. to 32° C., and grows well at from 17° C. to 26° C. Other temperatures not falling within these ranges may be applicable where a strain has been developed which can grow at lower or higher temperatures. For the production of thiomarinol B and/or C, a preferable temperature is between 20° C. and 26° C.

Thiomarinol B and/or C is ideally obtained by aerobic culture, and any suitable aerobic culture techniques, such as, for example, solid culture, shaking culture or aeration-agitation culture may be employed.

If the culture is conducted on a small scale, then a shaking culture fermented for several days at from 20° C. to 26° C. is generally preferred.

To start a fermentative culture, a preferred technique employs an initial inoculum prepared in one or two steps, in an Erlenmeyer flask, for example. A carbon source and a nitrogen source may be used in combination for the culture medium. The seed flask is shaken in a thermostatic incubator at 23° C. for 1 to 3 days, or until sufficient growth is observed. The resulting seed culture may then be used to inoculate a second seed culture, or a producing culture. If a second seeding is conducted, this may be performed in a similar manner, and partly used for inoculation to the production medium. The flask into which the seed is inoculated is shaken for a suitable period, for example from 1 to 3 days, or until maximal production is obtained, at a suitable temperature, for example as described above. When incubation is complete, the contents of the flask may be collected by centrifugation or filtration.

If the culture is performed on a large scale, culture in a suitable aeration-agitation fermenter may be preferable. In this procedure, the nutrient medium can be prepared in a fermenter. After sterilizing at 125° C., the medium is cooled and seeded with an inoculum previously grown on a sterilized medium. The culture is performed at 20° C. to 26° C. with stirring and aeration. This procedure is suitable for obtaining a large amount of the compound.

The amount of thiomarinol B and/or C produced by the culture with the passage of time can be monitored by high performance liquid chromatography, for example. In general, the amount of thiomarinol B produced reaches a maximum after a period of time between 19 hours and 200 hours, and the amount of thiomarinol C produced reaches a maximum after a period of time between 19 hours and 200 hours; in contrast, the amount of thiomarinol produced reaches a maximum after a period of time between 19 hours and 96 hours.

After a suitable period of culture, the thiomarinol B and/or C may be isolated and purified by any known means. For example, any thiomarinol B and/or C remaining in the culture broth may be obtained by filtering off the solids, for example, using diatomire as a filtration aid, or by centrifugation and subsequent extraction from the supernatant by purification according to the physico-chemical properties of thiomarinol B or C. For example, thiomarinol B and/or C existing in the filtrate or in the supernatant can be extracted with a water-immiscible organic solvent such as ethyl acetate, chloroform, ethylene chloride, methylene chloride or any mixture thereof, under neutral or acidic conditions, and purified.

Alternatively, as an adsorbent, active carbon or an adsorbing resin such as Amberlite (trade mark) XAD-2, XAD-4 (Rohm & Haas) or Diaion (trade mark) HP-10, HP-20, CHP-20, HP-50 (Mitsubishi Kasei Corporation) may be employed. Impurities can be removed after adsorption by passing the liquid containing the thiomarinol B and/or C through a layer of the adsorbent; or thiomarinol B and/or C can be purified after adsorption by elution with a suitable eluent, such as aqueous methanol, aqueous acetone or butanol/water.

Intracellular thiomarinol B and/or C may be purified by extraction with a suitable solvent, such as aqueous acetone or aqueous methanol, preferably having a concentration of from 50 to 90% by volume, subsequently removing the organic solvent, followed by extraction as described above for the filtrate or supernatant.

The resulting thiomarinol B and/or C may be further purified by well known techniques, for example: adsorption column chromatography using a carrier, such as silica gel or magnesium-silica gel, for example that sold under the trade name "Florisil"; partition column chromatography using an adsorbent such as Sephadex LH-20 (a trade name for a product of Pharmacia); or high performance liquid chromatography using a normal phase or reverse phase column. As is well known in the art, these isolation and purification procedures may be carried out alone or in any suitable combination, and, if desired, repeatedly, to isolate and purify the desired final product.

Alternatively, thiomarinol B may be prepared by oxidation of thiomarinol, and this process is considered advantageous, as thiomarinol B is obtained only in relatively minor amounts by fermentation.

The oxidation is preferably effected by allowing an oxidizing agent to act on thiomarinol in the presence of a solvent and in the presence or absence of a base.

The nature of the oxidizing agent used is not critical to the process of the present invention, and any oxidizing agent commonly used in oxidization reactions may equally be used here. Examples of such oxidizing agents include: potassium permanganate; chromates, such as potassium dichromate (potassium bichromate), sodium dichromate (sodium bichromate), chrome oxide (VI), chromyl chloride and t-butyl chromate; ruthenium tetroxide; halogens, such as chlorine, bromine and iodine; ozone; oxygen; hydrogen peroxide; organic peroxides, such as bis(trimethylsilyl) peroxide, cumyl hydroperoxide and t-butyl hydroperoxide; dioxiranes, such as dioxirane, methyl dioxirane, dimethyl dioxirane, diethyl dioxirane, ethyl methyl dioxirane, methyl propyl dioxirane, butyl methyl dioxirane, fluorodioxirane, methyl fluorodioxirane, difluorodioxirane, bis(trifluoromethyl) dioxirane, methyl trifluoromethyl dioxirane and trifluoromethyl chlorodifluoromethyl dioxirane; organic peracids and salts thereof, such as peracetic acid, performic acid and m-chloroperbenzoic acid; and peroxysulfuric acids and salts thereof, such as peroxymonosulfuric acid, potassium peroxydisulfate and potassium peroxymonosulfate (particularly that sold under the trade name "Oxone", a product of Aldrich Chemical Co.). Preferred examples of oxidizing agents include hydrogen peroxide, organic peracids and salts thereof, organic peroxides, dioxiranes and peroxysulfuric acids and salts thereof, and particularly preferred examples include hydrogen peroxide, dimethyl dioxirane and peroxysulfuric acids and salts thereof.

There is likewise no particular restriction on the nature of the base employed in this reaction, provided that it has no adverse effect on the reaction or on the reagents. Preferred examples of such bases include: inorganic salts, for example carbonates of alkali metals (such as sodium carbonate, potassium carbonate or lithium carbonate), hydrogencarbonates of alkali metals (such as sodium hydrogencarbonate, potassium hydrogencarbonate or lithium hydrogencarbonate), hydrides of alkali metals (such as lithium hydride, sodium hydride or potassium hydride), hydroxides of alkali metals (such as sodium hydroxide, potassium hydroxide, barium hydroxide or lithium hydroxide) and fluorides of alkali metals (such as sodium fluoride, potassium fluoride or cesium fluoride); organic salts, for example alkoxides of alkali metals (such as sodium methoxide, sodium ethoxide, potassium t-butoxide or lithium methoxide), alkali metal alkyl sulfides (such as sodium methyl sulfide or sodium ethyl sulfide); and nitrogen compounds (such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Particularly preferred examples include carbonates of alkali metals and hydrogencarbonates of alkali metals.

The reaction is normally and preferably carried out in the presence of a solvent, the nature of which is not critical, provided that it has no adverse effect upon the reaction and that it can dissolve the reagents, at least to some extent. Examples of suitable solvents include: water; alcohols, such as methanol, ethanol or propanol; ketones, such as acetone or methyl ethyl ketone; organic acids, such as acetic acid or formic acid; esters, such as ethyl acetate; ethers, such as diethyl ether or tetrahydrofuran; amides, such as dimethylformamide or dimethylacetamide; and mixtures of any two or more of these solvents. Preferred examples include alcohols and mixtures of water and ketones, while particularly preferred examples include a mixture of water and acetone.

If desired, the reaction may be carried out in the presence of an inorganic catalyst, such as platinum oxide or vanadium oxide, in order to facilitate the reaction, although the reaction will proceed without such catalysts.

The reaction will take place over a wide range of temperatures, and the precise reaction temperature chosen is not critical to the invention. In general, we find it convenient to carry out the reaction at a temperature in the range of from −78° C. to 100° C., more preferably from −10° C. to room temperature. The time required for the reaction may likewise vary widely, depending on many factors, notably the reaction temperature and the nature of the reagents, particularly the oxidizing agent and the base employed. However, in most cases, a period of from 15 minutes to 30 hours, more preferably from 15 minutes to 2 hours, will normally suffice.

After completion of the reaction, the desired compound may be recovered from the reaction mixture by conventional means. For example, one suitable recovery technique comprises: pouring the reaction mixture into water; extracting it with a solvent immiscible with water, such as an aromatic hydrocarbon (for example benzene), an ether (for example diethyl ether), an ester of an organic acid (for example ethyl acetate) or a halogenated hydrocarbon (for example methylene chloride); and then distilling off the solvent from the extract. The desired compound obtained in this manner can, if desired, be further purified by conventional methods, for example using the various chromatography techniques, notably column chromatography or preparative thin layer chromatography.

Thiomarinol, which is the starting material for this oxidation reaction can be prepared by fermentation using a microorganism of the genus genus Alteromonas, especially *Alteromonas rava* strain SANK 73390, as described above in relation to the preparation of thiomarinol B and C.

As thiomarinols B and C exhibit an antibacterial effect against gram-positive and gram-negative bacteria and mycoplasma in animals (e.g. human, dog, cat and rabbit), they can be used for the treatment or prophylaxis of bacterial or mycoplasmal infections by various routes, depending upon the nature of the infection.

When the compounds of the invention are intended for therapeutic use, they may be administered alone or in a suitable pharmaceutical formulation containing, in addition to the active compound, one or more conventional diluents, carriers, excipients or adjuvants. The nature of the formulation will, of course, depend on the intended route of administration. However, for the oral route, the compound is preferably formulated as powders, granules, tablets, capsules or syrups. For parenteral administration, it is preferably formulated as an injection (which may be intravenous, intramuscular or subcutaneous), as drops, suppositories, ointments or liniments.

These formulations can be prepared by known means by adding to the active compound such additives as vehicles, binders, disintegrators, lubricants, stabilizers, corrigents, solubilizing agents, flavorings, perfumes, suspending agents or coating agents. Although the dosage may vary depending upon the symptoms and age of the patient, the nature and severity of the infection and the route and manner of administration, in the case of oral administration to an adult human patient, the compounds of the present invention may normally be administered at a daily dose of from 20 mg to 2000 mg. The compounds may be administered in a single dose, or in divided doses, for example two or three times a day.

The preparation of the compounds of the present invention is further illustrated by the following non-limiting Examples, and the biological activities of these compounds are illustrated by the subsequent Test Examples. Example 6 illustrates the preparation of thiomarinol, which is used as a starting material for the oxidative preparation of thiomarinol B.

EXAMPLE 1

PREPARATION OF THIOMARINOL B BY CULTURING IN A TANK

A) Culture

*Alteromonas rava* strain SANK 73390 was cultured for 3 days at 22° C. on a slant of Marine Agar (a product of Difco). The resulting culture was suspended in 3 ml of sterilized artificial sea water. 0.1 ml of the resulting suspension was inoculated into each of two 500 ml Erlenmeyer flasks each containing 100 ml of a sterilized medium having the following composition:

| Marine Broth (Difco) | 37.4 g |
|---|---|
| Deionized water | 1000 ml |
| pH not adjusted | |

The culture was then incubated for 24 hours at 23° C. with shaking at 210 rpm, using a rotary shaker. The whole of the resulting culture was then inoculated into a 600 liter aerated stir-culture tank containing 200 liters of a medium having the same composition as described above, which had been sterilized separately. This was then cultured at 23° C. for 26 hours, whilst aerating the culture at an air flow rate of 0.5 vvm (i.e. "volume per volume per minute": 1 vvm means that the amount of air supplied in one minute is equal to the volume of the air in the tank), and adjusting the speed of rotation to within the range of from 82.5 to 170 rpm to maintain the dissolved oxygen concentration at 5.0 ppm.

B) Isolation

Sufficient aqueous hydrochloric acid was added to 230 liter of the resulting culture solution to adjust its pH to a value of 2.5. 200 liters of acetone were then added to the resulting mixture, and the mixture was extracted, with stirring, for 0.5 hour. 4.0 kg of Celite 545 filter aid (a trade mark for a product of Jones Manvill Project Corporation, U.S.A.) were then added to the mixture, and the mixture was filtered. The filtrate (430 liters) was extracted once with 200 liters of ethyl acetate and then twice with 100 liter of ethyl acetate. The combined ethyl acetate extracts were washed with 200 liters of a 5% w/v aqueous solution of sodium hydrogencarbonate and then with 100 liters of a saturated aqueous solution of sodium chloride, after which they were dried over anhydrous sodium sulfate, and then evaporated to dryness under reduced pressure, to give approximately 80 g of an oil.

The whole of the oil thus obtained was dissolved in methylene chloride, and the resulting solution was adsorbed onto a column packed with 1.1 kg of silica gel, which had been saturated with methylene chloride. The solution was then eluted with a 1:1 by volume mixture of methylene chloride and ethyl acetate, with ethyl acetate alone and with a 9:1 by volume mixture of ethyl acetate-methanol, in that order (the polarity of the eluents increases in this order). After the eluate had been fractionated into aliquots of 500 ml each, the fraction containing thiomarinol B, eluted with the mixture of ethyl acetate and methanol was collected and evaporated to dryness under reduced pressure, to give 60 g of an oil.

The whole of the resulting oil was dissolved in 6 liters of 50% v/v aqueous methanol, and the resulting solution was adsorbed onto a 2.3 liter column packed with Diaion HP-20 (trade mark) which had been saturated with water, after which the solution of the oil was subjected to stepwise gradient elution using aqueous methanol, where the concentration of the methanol was gradually increased from 30% to 90% by volume. More specifically, after 4 liter each of 30% aqueous methanol, 50% aqueous methanol, 60% aqueous methanol, 70% aqueous methanol and 80% aqueous methanol had been applied to the column, the column was eluted with 90% aqueous methanol. Elution was continued until no more elution of the compound is observed, as monitored by high performance liquid chromatography, the amount of 90% aqueous methanol used for elution being approximately 10 liters. The fraction eluted with 90% aqueous methanol was collected and evaporated to dryness under reduced pressure, to give 3.8 g of a yellow powder. The yellow powder was subjected to chromatography using a column packed with 320 g of Sephadex LH-20 which had been saturated with a 19:19:2 by volume mixture of methylene chloride, ethyl acetate and methanol, after which it was eluted with the same solvent mixture, to effect purification.

The resulting product was further purified by high performance liquid chromatography, using a reverse phase column [Senshu-Pak ODS H-5251 (Column size: 20 mm diameter, 250 mm long), a trade mark for a product of Senshu Scientific Co., Ltd.] and using 40% v/v aqueous acetonitrile as the eluent at a flow rate of 15 ml/minute, to purify the product, whilst monitoring the purification by observing the absorbance at 220 nm. Since thiomarinol B was obtained as a peak with a retention time of from 13 to 14 minutes, this fraction was collected and evaporated to dryness under reduced pressure, to isolate 130 mg of the title compound having the physico-chemical properties listed previously.

EXAMPLE 2

PREPARARION OF THIOMARINOL B BY OXIDIZING THIOMARINOL 100.9 mg of thiomarinol (prepared as described in Example 6) were dissolved in a mixture of 5 ml of acetone and 5 ml of water, and then the resulting solution was ice-cooled. 112.2 mg of OXONE (a trade name for a product of Aldrich Chemical Co., Inc.) were added to the resulting solution, and then the mixture was stirred, whilst ice-cooling, for 40 minutes. At the end of this time, 1.2 ml of a saturated aqueous solution of sodium hydrogencarbonate were added to this mixture, and the mixture was again stirred, whilst ice-cooling, for 30 minutes. 5 ml of water were then added to the reaction mixture, which was then extracted with a 10:1 by volume mixture of methylene chloride and tetrahydrofuran. The extract was dried over anhydrous sodium sulfate, and then the solvent was removed by distillation under reduced pressure. The resulting residue was then isolated and purified by reverse phase, high performance liquid chromatography (using a Senshu Pak ODS-5251-N column, and 40% v/v aqueous acetonitrile as the eluent), to obtain 79.5 mg (yield 75%) of thiomarinol B having a light yellow color and having the physico-chemical properties listed above.

EXAMPLE 3

PREPARATION OF THIOMARINOL B BY OXIDIZING THIOMARINOL 100 mg of thiomarinol (prepared as described in Example 6) were dissolved in a mixture of 15 ml of acetone and 7.5 ml of water, and then 0.074 ml of 35% aqueous hydrogen peroxide and 2 drops of a dilute aqueous solution of sodium hydrogencarbonate were added to the mixture. The reaction mixture was stirred for 5 minutes, after which the acetone was removed by distillation under reduced pressure. Acetonitrile was then added to the residue, and the formation of thiomarinol B was confirmed by reverse phase high performance liquid chromatography (using a Senshu Pak ODS-H-2151 column, and 40% v/v aqueous acetonitrile as the eluent). The solvent was removed from the reaction mixture by distillation under reduced pressure, and the resulting residue was dissolved in 40% v/v aqueous acetonitrile. It was then isolated and purified by reverse phase high performance liquid chromatography (using a Senshu Pak ODS-4251-N column, and 40% v/v aqueous acetonitrile as the eluent), to obtain 43.2 mg (yield 41%) of thiomarinol B having a light yellow color and having the physico-chemical properties listed above.

EXAMPLE 4

PREPARATION OF THIOMARINOL B BY OXIDIZING THIOMARINOL 100 mg of thiomarinol (prepared as described in Example 6) were dissolved in 40 ml of acetone, and then 134 mg of m-chloroperbenzoic acid were added, whilst ice-cooling and stirring, to the resulting solution. The mixture was then stirred for 1.5 hours at room temperature. At the end of this time, the reaction mixture was extracted with methylene chloride, and the extract was washed three times with water and then once with saturated aqueous solution of sodium hydrogensulfate. The extract was dried over anhydrous sodium sulfate, after which the solvent was removed by distillation under reduced pressure. The resulting residue was isolated and purified by reverse phase high performance liquid chromatography (using a Senshu Pak ODS-4251-N column, and 40% v/v aqueous acetonitrile as the eluent), to obtain 8.5 mg (yield 8%) of thiomarinol B having a light yellow color and having the physico-chemical properties listed above.

EXAMPLE 5

PREPARATION OF THIOMARINOL C BY CULTURING IN A TANK

A) Culture

One slant of Marine Agar (Difco) to which *Alteromonas rava* strain SANK 73390 had been applied and grown was added to 10 ml of a sterilized Marine Broth (Difco) to prepare a bacterium suspension.

A 30 liter jar fermenter containing 15 liters of the same Marine Broth medium was sterilized by heating, and then the whole of the bacterium suspension was inoculated into the fermenter, and cultured at a temperature of 23° C. and at an air flow rate of 7.5 liters/minute for 24 hours. The initial stirring speed was 100 rpm and then the stirring speed was adjusted appropriately, in order to maintain the dissolved oxygen concentration at 5.0 ppm.

300 liters of a culture medium having the following composition were then charged into each of two 600 liter tanks:

| | |
|---|---|
| Glucose | 1.5% |
| Bactopeptone (Difco) | 1.5% |
| Bactoyeast extract (Difco) | 0.2% |
| NaCl | 3.89% |
| MgCl$_2$.6H$_2$O | 2.52% |
| Na$_2$SO$_4$ | 0.648% |
| CaCl$_2$.2H$_2$O | 0.4767% |
| KCl | 0.11% |
| Na$_2$CO$_3$ | 0.038% |
| Ferric citrate | 0.02% |
| pH 7.6 before sterilization | |

The tanks were then sterilized by heating, after which 3 liters of the seed culture were inoculated into each tank, and cultured at a temperature of 23° C. and at an air flow rate of 150 liters/minute for 29 hours. The initial stirring speed was 82 rpm and then the stirring speed was adjusted appropriately, in order to maintain the dissolved oxygen concentration at 5.0 ppm.

B) Isolation

Sufficient aqueous hydrochloric acid was added to 700 liters of the resulting culture solution to adjust its pH to a value of 3, and then 700 liters of acetone were added to the resulting mixture, and extraction was carried out, with stirring, for 1 hour. The resulting extract was itself then extracted once with 700 liters of ethyl acetate and then once with 300 liters of ethyl acetate. The combined ethyl acetate extracts were then washed with 300 liters of a 5% w/v aqueous solution of sodium hydrogencarbonate and with 300 liters of a saturated aqueous solution of sodium chloride, in that order, after which they were dried over anhydrous sodium sulfate. The solvent was then removed by evaporation under reduced pressure. In the course of the evaporation procedure, 540 g of silica gel were added, and then evaporation to dryness was continued.

The residue thus obtained was suspended in methylene chloride, and the resulting solution was charged onto a column packed with 4 kg of silica gel saturated with methylene chloride. It was then eluted with methylene chloride, with a 1:1 by volume mixture of methylene chloride and ethyl acetate, with ethyl acetate alone and with a 9:1 by volume mixture of ethyl acetate and methanol, in that order; the polarity of the eluents increases in this order. The eluate was fractionated into aliquots of 2 liters each, and the fraction containing thiomarinol C, which was eluted with the mixture of ethyl acetate and methanol was collected and evaporated to dryness under reduced pressure. In the course of the evaporation procedure, 50 g of silica gel were added, and then evaporation to dryness was continued.

The resulting residue was suspended in a mixture of hexane and acetone, and the resulting suspension was charged onto a column packed with 200 g of silica gel saturated with hexane, which was then eluted with a 1:1 by volume mixture of hexane and acetone. The eluate was fractionated into aliquots of 500 ml each to obtain fractions 1 and 2 containing thiomarinol C. Fraction 1 was concentrated by evaporation under reduced pressure. In the course of the concentration procedure, 25 g of silica gel were added, and then evaporation to dryness was continued.

The resulting residue was suspended in a 1:1:2 by volume mixture of hexane, acetone and ethyl acetate, and the resulting suspension was charged onto a column packed with 200 g of silica gel saturated with hexane. It was then eluted with a 1:1:2 by volume mixture of hexane, acetone and ethyl acetate. The eluate was fractionated into aliquots of 500 ml each, and the fraction containing thiomarinol C was saved. This fraction was combined with the fraction 2 obtained above, and the combined fractions were concentrated by evaporation under reduced pressure. In the course of the concentration procedure, 20 g of silica gel were added, and then evaporation to dryness was continued.

The resulting residue was suspended in a 1:1:1 by volume mixture of hexane, acetone and ethyl acetate, and the resulting suspension was charged onto a column packed with 200 g of silica gel saturated with hexane. It was then eluted with a 1:1:1 by volume mixture of hexane, acetone and ethyl acetate. The eluate was fractionated into aliquots of 500 ml each, and the fractions containing thiomarinol C were collected and concentrated by evaporation under reduced pressure, to obtain an oily substance.

The whole of this oily substance was further subjected to chromatography using a 200 ml column packed with Sephadex LH-20 saturated with a 19:19:2 by volume mixture of methylene chloride, ethyl acetate and methanol, and was purified by elution with the same solvent mixture. The fractions containing thiomarinol C were collected and concentrated by evaporation under reduced pressure. In the course of the concentration procedure, 25 g of silica gel were added, and then evaporation to dryness was continued.

The resulting residue was suspended in methylene chloride, and the suspension was charged onto a column packed with 250 g of silica gel saturated with methylene chloride. It was then eluted with mixtures of methylene chloride and acetone, in proportions varying from 9:1 to 1:9 by volume, so that the polarity of the eluent gradually increased. The eluate was fractionated into aliquots of 1 liter each, and the fractions containing thiomarinol C were collected and evaporated to dryness under reduced pressure to isolate 150 mg of thiomarinol C, having the physico-chemical properties listed above.

EXAMPLE 6

JAR FERMENTATION OF THIOMARINOL

A) Culture

*Alteromonas rava* strain SANK 73390 was cultured for days at 22° C. on a slant of Marine Agar (a product of Difco). The resulting culture was suspended in 3 ml of artificial sea water. 0.1 ml of the suspension was taken aseptically and inoculated into a 500 ml Erlenmeyer flask containing 100 ml of sterilized medium 37.4 g Marine Broth (product of Difco) in 1 liter of deionised water, pH not adjusted].

The flask was incubated for 24 hours at 23° C. with shaking at 200 rpm (rotation radius of 70 mm), using a rotary shaker. After this time, each of four 30 liter jar fermenters, each containing 15 liters of the sterile medium described above, was inoculated with 15 ml of culture taken aseptically from the Erlenmeyer flask. The jar fermenters were incubated for 23 hours at 23° C., at an aeration rate of 7.5 liters/minute, with stirring (100 rpm).

B) Isolation

After 23 hours, the contents of the fermenters were combined to yield 60 liters of culture liquid. The pH of the liquid was then adjusted to a value of 3 by the addition of hydrochloric acid, after which 60 liters of acetone were added, and the mixture was extracted for 30 minutes, whilst stirring. Using 1.2 kg of Celite 545 filter aid (a trade mark of a product obtainable from Johns Manville Co.), the solution was filtered. 110 liters of the resulting filtrate were then extracted once with 60 liters of ethyl acetate, and twice with ethyl acetate, each time with 30 liters. The combined organic extracts were washed with 30 liters of a 5% w/v aqueous solution of sodium hydrogencarbonate, and subsequently with 30 liters of saturated aqueous sodium chloride solution. The mixture was then dried over anhydrous sodium sulfate, and evaporated to dryness under reduced pressure, to obtain 14 g of an oily substance.

The whole of the oily substance obtained was dissolved in methylene chloride, and the solution was adsorbed on a column packed with 200 g of silica gel which had been saturated with methylene chloride. The solution was then eluted with a 1:1 by volume mixture of methylene chloride and ethyl acetate, with ethyl acetate alone and with a 9:1 by volume mixture of ethyl acetate-methanol, in that order (the polarity of the eluents increases in this order). The eluent was collected in fractions of 18 ml, and the fractions eluted with a mixture of ethyl acetate and methanol, which contained thiomarinol, were saved.

The saved fractions were evaporated to dryness, to obtain 7 g of an oily substance, which was dissolved in 400 ml of 50% v/v aqueous methanol and adsorbed on 600 ml of a column packed with Diaion HP-20 (a trade mark of a product obtainable from Mitsubishi Chem. Ind.) which had been saturated with water. The column was washed with 50% v/v aqueous methanol, and then the target substance was eluted with 90% v/v aqueous methanol. 1 g of a yellow powder was obtained from the resulting fraction by evaporation under reduced pressure. This yellow powder was further eluted on a column chromatogramusing Sephadex LH-20, and developed with a 19:19:2 by volume mixture of methylene chloride, ethyl acetate and methanol. 750 mg of thiomarinol was obtained as a yellow powder from the active fractions.

The resulting thiomarinol had the properties shown below.

1) Nature and appearance: Yellow powder.
2) Melting point: 84°–89° C.
3) Molecular formula: $C_{30}H_{44}N_2O_9S_2$.
4) Molecular weight: 640, determined by FAB-MS method ("FAB-MS" is Fast Atom Bombardment Mass Spectrometry).
5) High resolution mass spectrum: $C_{30}H_{45}N_2O_9S_2$ [$(M+H)^+$ by FAB-MS method]: Calculated: 641.2567 Found: 641.2585.
6) Elemental analysis: Calculated: C, 56.23%; H, 6.92%; N, 4.37%; S, 10.01% Found: C, 55.92%; H, 6.82%; N, 4.23%; S, 9.90%
7) Infrared absorption spectrum: the infrared spectrum showed the following absorption maxima (KBr disc method, $\nu_{max}$ cm$^{-1}$):
3394, 2930, 1649, 1598, 1526, 1288, 1216, 1154, 1102, 1052.
8) Ultraviolet absorption spectrum:
In methanol, or methanol+HCl, thiomarinaol has the ulraviolet absorption spectrum shown below: [given as $\nu_{max}$ nm ($\epsilon$)]
387 (12,000), 300 (3,500), 214 (26,000) and in methanol+NaOH has the ultraviolet spectrum shown below: [given as $\nu_{max}$ nm ($\epsilon$)]
386 (9,600), 306 (3,200), 206 (25,000).
9) Specific rotation: $[\alpha]_D^{25} = +4.3°$ (C=1.0, methanol).
10) High performance liquid chromatography:
Separating column: Senshu-Pak ODS H-2151 (Column size, 6×150 mm, Product of Senshu Scientific Co., Ltd.)
Solvent: 40% v/v aqueous acetonitrile
Flow rate: 1.5 ml/minute
Wave length: 220–350 nm (detected by photodiode array)
Retention time: 5.9 minutes.
11) $^1$H-Nuclear magnetic resonance spectrum: ($\delta$ ppm) the Nuclear magnetic resonance spectrum (270 MHz) in hexadeuterated dimethyl sulfoxide, using tetramethylsilane as the internal standard, is shown below:
0.91 (3H, doublet, J=6.8 Hz);
0.95 (3H, doublet, J=5.9 Hz);
1.30 (6H, broad multiplet);
1.55 (5H, broad multiplet);
2.03 (3H, singlet);
2.09 (3H, multiplet);
2.34 (2H, triplet, J=7.3 Hz);
3.33 (1H, doublet, J=10.7 Hz);
3.52 (2H, multiplet);
3.64 (2H, multiplet);
3.73 (1H, doublet of doublets);
4.02 (2H, triplet, J=6.6 Hz);
4.18 (1H, broad doublet, J=7.3 Hz);
4.30 (1H, doublet, J=4.4 Hz);
4.44 (1H, doublet, J=7.8 Hz);
4.63 (1H, doublet, J=3.4 Hz);
4.89 (1H, doublet, J=7.3 Hz);
5.37 (2H, multiplet);
5.97 (1H, broad singlet);
7.04 (1H, singlet);
9.80 (1H, broad singlet);
10.68 (1H, broad singlet).
12) $^{13}$C-Nuclear magnetic resonance spectrum:
($\delta$ ppm): the nuclear magnetic resonance spectrum (68 MHz) in tetradeuterated methanol, using tetramethylsilane as the internal standard, is shown below:
174.3 (singlet), 170.4 (singlet), 168.6 (singlet),
161.1 (singlet), 137.9 (singlet), 135.7 (doublet),
135.1 (singlet), 129.8 (doublet), 116.3 (doublet),
115.8 (singlet), 113.7 (doublet), 77.6 (doublet),
74.4 (doublet), 72.1 (doublet), 71.8 (doublet),
66.0 (triplet), 65.7 (doublet), 64.9 (triplet),
45.3 (doublet), 43.9 (doublet), 36.6 (triplet),
33.4 (triplet), 30.1 (triplet), 30.0 (triplet),
29.7 (triplet), 27.0 (triplet), 26.7 (triplet),
20.3 (quartet), 16.6 (quartet), 16.3 (quartet).
13) Solubility:
Soluble in alcohols such as methanol, ethanol, propanol and butanol; and soluble in dimethyl sulfoxide, dimethylformamide, chloroform, ethyl acetate, acetone and diethyl ether; insoluble in hexane and water.
14) Color reactions:
Positive to sulfuric acid, iodine and potassium permanganate.
15) Thin layer chromatography:
$R_f$ value: 0.57
Adsorbing agent: Silica gel (Merck & Co. Inc., Art. 5715)
Developing solvent: methylene chloride: methanol=85:15 by volume.

BIOLOGICAL ACTIVITY

The biological activity of thiomarinols B and C is demonstrated by the following Test Examples, in which they are compared with pseudomonic acid A and thiomarinol.

TEST EXAMPLE 1

ANTIBACTERIAL ACTIVITY OF THIOMARINOLS B AND C

The minimum inhibitory concentration (MIC) of thiomarinol, thiomarinol B, thiomarinol C and pseudomonic acid A (identified as "A", "B", "C" and "P", respectively) given as μg/ml, against gram-positive and gram-negative bacteria was determined by the agar medium dilution method, using a nutrient agar medium (Product of Eiken Chemical Co., Ltd.).

The results are given in Table 1 below.

TABLE 1

| | MIC (μg/ml) | | | |
|---|---|---|---|---|
| Test bacterial strain | A | B | C | P |
| Staphylococcus aureus 209P | ≦0.01 | ≦0.01 | ≦0.01 | 0.05 |
| Staphylococcus aureus 56R | ≦0.01 | ≦0.01 | ≦0.01 | 0.1 |
| Staphylococcus aureus 535 (MRSA) | ≦0.01 | ≦0.01 | ≦0.01 | 0.2 |
| Enterococcus faecalis 681 | 0.02 | 0.05 | 0.8 | 25 |
| Escherichia coli NIHJ | 0.8 | 0.8 | 3.1 | 100 |
| Escherichia coli 609 | 0.8 | 0.8 | 1.5 | 100 |
| Salmonella enteritidis | 0.4 | 0.4 | 1.5 | 50 |
| Klebsiella pneumoniae 806 | 0.8 | 0.8 | 1.5 | 100 |
| Klebsiella pneumoniae 846 (R) | 0.2 | 0.2 | 0.8 | 100 |
| Enterobacter cloacae 963 | 1.5 | 0.8 | 3.1 | >100 |
| Serratia marcescens 1184 | 3.1 | 3.1 | 6.2 | >100 |
| Proteus vulgaris 1420 | 0.05 | 0.05 | 0.2 | 0.4 |
| Morcranella morganii 1510 | 6.2 | 6.2 | 12.5 | >100 |
| Pseudomonas aerucrinosa 1001 | 0.2 | 0.2 | 0.8 | >100 |
| Pseudomonas aerucrinosa No. 7 | 0.4 | 0.4 | 0.8 | >100 |
| Pseudomonas aeruginosa 3719 | — | 0.8 | 0.4 | >100 |

TEST EXAMPLE 2

ANTIMYCOPLASMAL ACTIVITY OF THIOMARINOLS B AND C

Following the same procedure as for Test Example 1, the activity of thiomarinol, thiomarinol B, thiomarinol C and pseudomonic acid A (identified as "A", "B", "C" and "P", respectively) was assayed against various species of mycoplasma. The results are given in Table 2, below.

TABLE 2

| | MIC (μg/ml) | | | |
|---|---|---|---|---|
| Test mycoplasmal strain | A | B | C | P |
| Mycoplasma hyosynoviae S-16 | 0.025 | | | |
| Mycoplasma hyorhinis BTS 7 | | 0.78 | 1.56 | 0.39 |

Inoculum: 0.005 ml of $10^5$ CFU/ml
Media for assay:
  Thiomarinol B, Thiomarinol C and Pseudomonic acid A were all assayed on Chanock medium [prepared as described in P.N.A.S., 48, 41–49 (1962) and supplemented with 20% horse serum] for all microorganisms;
  Thiomarinol was assayed on the following media:
  M. bovis and M. gallisepticum: Chanock medium (prepared as described above)
  M. hyosynoviae: Mucin PPLO* agar medium (15% horse serum supplemented)

| *PPLO (Pleuro Pneumonia-Like Organism) | |
|---|---|
| PPLO Broth without CV (Difco) | 21 g |
| Mucin bacteriological (Difco) | 5 g |
| Distilled water | 800 ml |
| Agar Noble (Difco) | 12 g |
| Equine serum | 150 ml |
| 25% Fresh yeast extract | 50 ml |

Culture conditions: 37° C., 5 days, slightly aerobic (BBL gas pack method [cultivation in disposable $CO_2$ generator from Becton Dickinson Microbiology Systems, Cockeysville, Md. 2103 U.S.A.])

It is clear from the above results that thiomarinols B and C exhibit excellent antibacterial and anti-mycoplasmal activities, which are at least as good as those of thiomarinol and are, in general, significantly better than those of pseudomonic acid A.

We claim:

1. A compound named "thiomarinol C" and having the formula (C):

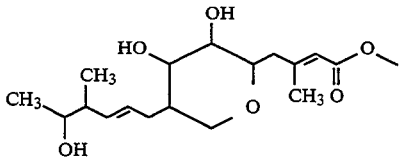

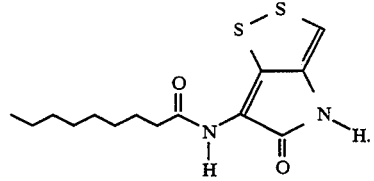

2. A composition of matter comprising the compound of claim 1 and a pharmaceutically acceptable carrier therefor.

3. A method for the treatment or prophylaxis of a bacterial infection, which method comprises administering an effective amount of the compound of claim 1 to a mammal suffering from or susceptible to such an infection.

4. The method of claim 3, wherein said mammal is human.

5. A compound named thiomarinol B and having the following formula:

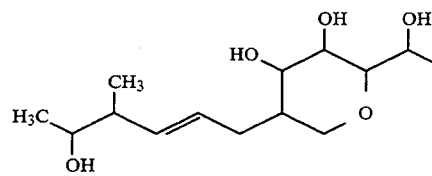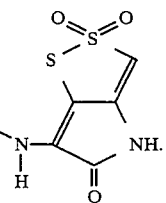

6. A composition of matter comprising the compound of claim 5 and a pharmaceutically acceptable carrier therefor.

7. A method for the treatment or prophylaxis of a bacterial infection, which method comprises administering an effective amount of the compound of claim 5 to a mammal suffering from or susceptible to such an infection.

8. The method of claim 7, wherein said mammal is human.

* * * * *

UNITED STATES PATENT AND TRADEMARK OFFICE
CERTIFICATE OF CORRECTION

PATENT NO. : 5,399,711
DATED : March 21, 1995
INVENTOR(S) : TAKAHASHI et al

Page 1 of 3

It is certified that error appears in the above-indentified patent and that said Letters Patent is hereby corrected as shown below:

Title page, left column, under "References Cited" insert

--U.S. PATENT DOCUMENTS 4,139,629    2/1979    Rogers    424/283--

Title page, right column, under "OTHER PUBLICATIONS" insert

-- Chain et al, "Pseudomonic Acid. Part 3. Structure of Pseudomonic Acid B", 1977, pp.318-322, J. Chem. Soc. Perkin Trans, I;

Clayton et al, "The Chemistry of Pseudomonic Acid. Part 5. Structure and Chemistry of Pseudomonic Acid C, X-Ray Crystal Structure of Ethyl Monate C, 1982, pp. 2827-2833, J. Chem Soc. Perkin Trans. I;

O'Hanlon et al, "The Chemistry of Pseudomic Acid. Part 6. Structure and Preparation of Pseudomonic Acid D", 1983, pp. 2655-2657, J. Chem. Soc. Perkin Trans. I;

Ettlinger et al, "Stoffwechselprodukte von Actinomyceten", 1959, pp. 563-569, Helv. Chem Acta, $\underline{42}$;

UNITED STATES PATENT AND TRADEMARK OFFICE
CERTIFICATE OF CORRECTION

PATENT NO. : 5,399,711
DATED : March 21, 1995
INVENTOR(S) : TAKAHASHI et al

Page 2 of 3

It is certified that error appears in the above-indentified patent and that said Letters Patent is hereby corrected as shown below:

Celmer et al, "The structures of Thiolutin and Aureothricin, Antibiotics Containing a Unique Pyrrolinonodithiole Nucleus", 1955, pp. 2861-2865, J. Am. Chem. Soc., 77;

Angew. Chem., 66, 745, 1954;

COMMUNICATIONS TO THE EDITOR, "Characterization of the Antibiotic Thiolutin and its Relationship with Aureothricin", 1952, pp. 6304-6305, J. Am. Chem. Soc., 74;

Abstracts of Papers from the 200 Year Conference of the Am. Chem. Soc. (August 26-31, 1990), Part 2, ORGN. No. 139;

Experimentia, Vol. 48, pp. 1165-1169 1992;

McInerney et al, "Biologically Active Metabolites from Xenorhabdus Spp., Part 1. Dithiolopyrrolone Derivatives with Antibiotic Activity", 1991, pp. 774-784, Journal of Natural Products, 54.

UNITED STATES PATENT AND TRADEMARK OFFICE
CERTIFICATE OF CORRECTION

PATENT NO. : 5,399,711
DATED : March 21, 1995
INVENTOR(S) : TAKAHASHI ET AL

It is certified that error appears in the above-indentified patent and that said Letters Patent is hereby corrected as shown below:

Column 21, TABLE 2, between lines 58 and 59, insert

| | | | | |
|---|---|---|---|---|
| --*Mycoplasma bovis* Donetta | 0.0125 | 0.006 | ≤0.006 | ≤0.006 |
| *Mycoplasma gallisepticum* PG-31 | 0.05 | 0.1 | 0.05 | 6.25 |
| *Mycoplasma gallisepticum* K-1 | 0.05 | 0.1 | 0.05 | 6.25-- |

Signed and Sealed this

Thirtieth Day of April, 1996

Attest:

BRUCE LEHMAN

Attesting Officer  Commissioner of Patents and Trademarks